US008741346B2

(12) United States Patent
Lochard et al.

(10) Patent No.: US 8,741,346 B2
(45) Date of Patent: Jun. 3, 2014

(54) METHOD FOR THE PREPARATION OF MOLECULAR COMPLEXES

(75) Inventors: Hubert Lochard, Albi (FR); Martial Sauceau, Saint Juery (FR); Bernard Freiss, Burlats (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 1443 days.

(21) Appl. No.: 10/554,058

(22) PCT Filed: Apr. 23, 2004

(86) PCT No.: PCT/FR2004/000995
§ 371 (c)(1),
(2), (4) Date: Oct. 24, 2005

(87) PCT Pub. No.: WO2004/096284
PCT Pub. Date: Nov. 11, 2004

(65) Prior Publication Data
US 2006/0246140 A1 Nov. 2, 2006

(30) Foreign Application Priority Data

Apr. 25, 2003 (FR) ...................................... 03 05140

(51) Int. Cl.
*A61K 48/00* (2006.01)
(52) U.S. Cl.
USPC ......................................................... 424/488
(58) Field of Classification Search
CPC .............................................. A61K 47/48969
USPC ......................................................... 424/488
See application file for complete search history.

(56) References Cited

U.S. PATENT DOCUMENTS

| | | | |
|---|---|---|---|
| 4,822,497 | A | 4/1989 | Hong et al. |
| 5,043,280 | A | 8/1991 | Fischer et al. |
| 5,073,267 | A | 12/1991 | Adda et al. |
| 5,389,263 | A | 2/1995 | Gallagher et al. |
| 5,700,482 | A | 12/1997 | Frederiksen et al. |
| 5,990,173 | A | 11/1999 | Patoiseau et al. |
| 6,107,284 | A | 8/2000 | Imbert et al. |
| 6,183,783 | B1 | 2/2001 | Benoit et al. |
| 6,414,050 | B1 | 7/2002 | Howdle et al. |
| 6,709,595 | B1 | 3/2004 | Perrut et al. |
| 2002/0189454 | A1 | 12/2002 | Perrut |

FOREIGN PATENT DOCUMENTS

| | | | |
|---|---|---|---|
| DE | 37 19 549 A1 | 12/1987 | |
| EP | 0 706 821 A1 | 4/1996 | |
| EP | 0 865 819 A1 | 9/1998 | |
| FR | 2 725 990 A1 | 4/1996 | |
| FR | 2 741 619 | 2/1998 | |
| FR | 2 798 863 A1 | 3/2001 | |
| FR | 2 799 984 A1 | 4/2001 | |
| FR | 2 830 760 A | 4/2003 | |
| GB | 2 191 715 A | 12/1987 | |
| GB | 2 252 059 | 7/1992 | |
| JP | 63141559 | 6/1988 | |
| JP | 4-290835 A | 10/1992 | |
| WO | WO-89/09639 A1 | 10/1989 | |
| WO | WO-95/01221 A1 | 1/1995 | |
| WO | WO-97/31691 A1 | 9/1997 | |
| WO | WO-98/13136 A1 | 4/1998 | |
| WO | WO-98/15348 A1 | 4/1998 | |
| WO | WO-99/25322 A2 | 5/1999 | |
| WO | WO-99/59710 A1 | 11/1999 | |
| WO | WO-00/27844 A1 | 5/2000 | |
| WO | WO-01/23064 A1 | 4/2001 | |
| WO | WO-01/28650 A1 | 4/2001 | |
| WO | WO-01/43853 | 6/2001 | |
| WO | WO-02/32462 A | 4/2002 | |
| WO | WO-02/083632 A | 10/2002 | |
| WO | WO-02/089851 | 11/2002 | |
| WO | WO 03/030867 | * 4/2003 | ............... A61K 9/14 |
| WO | WO-03/030867 A | 4/2003 | |

OTHER PUBLICATIONS

Machine translation of WO 03/030867 (Apr. 2003).*
Hess et al (Application of supercritical carbon dioxide for the preparation of a piroxicam-beta-cyclodextrin inclusion compound. Pharm Res. Dec. 1999;16(12):1864-70.*
Van Hees T. et al., "Application of Supercritical Carbon Dioxide for the Preparation of a Piroxicam-Beta-Cyclodextrin Inclusion Compound" Pharmaceutical Research, New York, NY, US, vol. 16, No. 12, Dec. 1999, pp. 1864-1870, XP001020308.
Van Hees T. et al., "Inclusion of Piroxicam Into Beta-Cyclodextrn by Means of Supercritical Carbon Dioxide: Thermal, Spectroscopic and Physicochemicals Studies" Journal de Pahrmacie de Belgique, Masson, Paris , FR, vol. 55, No. 1, Jan. 2000, pp. 30-31, XP001019795.
Kamihira M. et al., "Formation of Inclusion Complexes Between Cyclodextrins and Aromatic Compounds Under Pressurized Corbon Dioxide", Journal of Fermentation and Bioengineering, Society of Fermentation Technology, JP, vol. 69, No. 6, 1990, pp. 350-353, XP001020305.
Jung J. et al., "Particle design using supercritical fluids: Literature and patent survey" Journal of Supercritical Fluids, PRA Press, US, vol. 20, No. 3, Aug. 2001, pp. 179-219, XP004247117.
Bertucco et al. "Drugs encapsulation using a compressed gas antisolvent technique"—Proceedings of the 4th Italian Conference on Supeercritical Fluids and their Applications 1997, pp. 327-334—Ed. E. Reverchon.

(Continued)

*Primary Examiner* — Jake Vu
(74) *Attorney, Agent, or Firm* — Birch, Stewart, Kolasch & Birch, LLP

(57) ABSTRACT

The invention relates to a method for the preparation of soluble molecular complexes, comprising one or more active substances which are poorly-soluble in an aqueous medium, included within one or more host molecules, characterized in comprising the following steps: (a) bringing one or more active substances into contact with one or more host molecules, (b) carrying out a molecular diffusion step by bringing a dense fluid into contact, under pressure, with the mixture obtained in (a), in static mode, in the presence of one or more diffusion agents and (c) recovery of the molecular complex thus formed.

6 Claims, No Drawings

(56) References Cited

OTHER PUBLICATIONS

Chou et al., Gas crystallization of Polymer-pharmaceutical composite particles, Proceedings of the 4th International Symposium on Supercritical Fluids, 1997, p. 55-57.

Kim J.-H. et al., Microencapsulation of Naproxen using Rapid Expansion of Supercritical Solutions, Biotechnol. Prog. 1996, 12, p. 650-661.

Sze Tu et al. Application of dense gases in pharmaceutical processing, Proceedings of the 5th Meeting on Supercritical Fluids 1998, Tome 1, p. 263-269.

Weber et al. "Coprecipitation with compressed antisolvents for the manufacture of microcomposites, Proceedings of the 5th Meeting on Supercritical Fluids 1998", Tome 1, p. 243-248.

Bleich et Muller, Production of drug loaded by the use of supercritical gases with the erosal Solvent Extraction System(ASES) process, J. Microencapsulation 196, vol. 13, No. 2, p. 131-139, (1996).

Tom et al., "Applications of supercritical fluids in controlled release of drugs", Supercritical Fluids Engineering Science ACS Symp. Ser. 514, American Chemical Society, Washington DC, 1992.

Bala Subramaniam et al. "Pharmaceutical processing with supercritical carbon dioxid", Journal of Pharmaceutical Science. vol. 86, No. 8, Aug. 1997, p. 885-889.

Sze Tu L. et al. "Application of dense gazes in pharmaceutical processing", Proceedings of 5th meeting on supercritical fluids, Nice, France Mar. 1998.

Van Hees T. et al., "Inclusion of Piroxicam Into Beta-Cyclodextrn by Means of Supercritical Carbon Dioxide: Thermal, Spectroscopic and Physicochemicals Studies" Journal de Pharmacie de Belgique, Masson, Paris , FR, vol. 55, No. 1, Jan. 2000, pp. 30-31, XP001019795.

Kamihira M. et al., "Formation of Inclusion Complexes Between Cyclodextrins and Aromatic Compounds Under Pressurized Carbon Dioxide", Journal of Fermentation and Bioengineering, Society of Fermentation Technology, JP, vol. 69, No. 6, 1990, pp. 350-353, XP001020305.

Key Note K07, Lochard et al., "How to Inject Supercritical CO2 in a Pharmaceutical Project?", 9th International Symposium on SuperCritical Fluids 2009, Arcachon, France, May 18-20, 2009.

Lochard et al., "Use of Supercritical Fluid in Pharmaceutical Applications", 9th International Symposium on SuperCritical Fluids 2009, Arcachon, France, May 18-20, 2009.

De Zordi et al., "Piroxicam solid state studies after processing with SAS technique," J. of Supercritical Fluids, vol. 55, 2010, pp. 340-347.

Sauceau et al., "Solubility of eflucimibe in supercritical carbon dioxide with or without a co-solvent," J. of Supercritical Fluids, vol. 31, 2004, pp. 133-140.

Sovova et al., "High-pressure equilibrium of menthol + CO2," J. of Supercritical Fluids, vol. 41, 2007, pp. 1-9.

\* cited by examiner

METHOD FOR THE PREPARATION OF MOLECULAR COMPLEXES

The present invention relates to a method for the preparation of soluble molecular complexes by the technology of dense fluids under pressure, in particular that of $CO_2$.

High-value-added novel pharmaceutical molecules are in 40% of cases insoluble or poorly soluble in water, which hampers their bioavailability. Increasing the specific surface area of powders makes it possible to improve their rate of dissolution.

Now, the bioavailability of active ingredients may be considerably increased if their rate of dissolution is improved.

In the pharmaceutical, cosmetic and nutraceutical fields, a number of patent applications, patents and publications exist which relate to the formation, in a medium under pressure, of molecular complexes of an active substance in a coating substrate. Nevertheless, most of the methods described do not relate to the objective of improving the bioavailability, but rather the adsorption, of an active substance on a substrate.

Bertucco et al. (*Drugs encapsulation using a compressed gas antisolvent technique*—Proceedings of the 4th Italian Conference on Supercritical Fluids and their Applications 1997, 327-334—Ed. E. Reverchon) describe a method in which the active substance is suspended in a solution of biopolymer playing the role of the support. This suspension, placed in the autoclave, is then exposed to supercritical $CO_2$ in order to desolvate it (extraction of the solvent with supercritical fluid) and bring about the complexing of the support by super-saturation on the active substance. This method is a batch method in which the active substance is not precipitated by the supercritical fluid since it is in suspension. The structure of the particles of active substance is therefore unchanged, which does not contribute toward improving its dissolution in an aqueous medium.

A similar method is described by Benoit et al., in their patent application WO 98/13136.

Another technique for deposition of a support consists in solubilizing said support in the supercritical fluid, and then in precipitating this support on the active substance. To do this, the active substance and its support are placed beforehand in the stirred autoclave, and the injection of supercritical $CO_2$ solubilizes only the support (this implies that the support is soluble in the supercritical fluid and that the active substance is not), which is precipitated by modification of the pressure and temperature inside the autoclave. In this case, the initial structure of the active substance remains unchanged, and it is difficult to control the active substance/support ratio obtained in the complex precipitated. This batch method is detailed in patent application EP 706 821 by Benoit et al.

The microencapsulation method described by Shine and Gelb in their patent application WO 98/15348 consists in:
1. mixing an active substance with a polymer for encapsulation,
2. liquefying the polymer by passage of a stream of supercritical fluid,
3. rapidly depressurizing so as to solidify the polymer around the active substance.

This method is only applicable with an active substance and a polymer which are insoluble in the supercritical fluid. Because of this, the active substance preserves its original structure, which does not contribute toward improving its bioavailability.

In patent application FR2798863 by Perrut and Majewski, the active substance (kava-kava, turmeric, mixture of black pepper and sweet paprika), extracted beforehand with supercritical fluid, is precipitated in an auto-clave containing a porous support. The porous medium studied is maltodextrin. The authors claim a method for adsorbing the active substance on a porous medium, and not a phenomenon of diffusion of the active substance in the host molecule, making it possible to improve the dissolution of the molecular complex obtained.

A method for impregnating pharmaceutical active agents is claimed in patent application WO 99/25322 by Carli et al. It is as follows:
1. solubilization of the active ingredient with a supercritical fluid,
2. bringing the supercritical fluid containing the active ingredient into contact with the crosslinked polymer,
3. impregnation of the crosslinked polymer in static or dynamic mode,
4. elimination of the supercritical fluid.

Only active substances soluble in the supercritical fluid may be prepared by this method, since the first step consists in extracting the active ingredient with the supercritical fluid. Moreover, the method is not a method for inclusion but for impregnation on a support, and no result is given relating to the improvement in dissolution, in an aqueous medium, of the active ingredient thus prepared.

Van Hees et al. (*Application of supercritical carbon dioxide for the preparation of a Piroxicam-β-cyclodextrin inclusion compound*, Pharmaceutical Research, Vol. 16, No. 12, 1999) describe, in their publication, a method for the inclusion of piroxicam in β-cyclodextrins with supercritical $CO_2$. Piroxicam being poorly soluble in water, its inclusion in β-cyclodextrins should make it possible to increase its solubility in water. The method consists in placing a mixture of piroxicam and β-cyclodextrins in a reactor, left in static mode. After depressurizing, the mixture obtained is ground and homogenized before characterization by:

DSC (Differential Scanning Calorimetry),
measurement of solubility in acetonitrile and comparison with the solubility of piroxicam alone, and
spectroscopic methods.

DSC analysis makes it possible to conclude as to the complexing of piroxicam with β-cyclodextrin. Kamihira M. et al. (*J. of Fermentation and Bio-engineering*, Vol. 69, No. 6, 350-353, 1990) describe a method for the extraction of volatile aromatic compounds, and for trapping by inclusion in cyclodextrins. Geraniol and mustard oil are thus extracted with a supercritical fluid and then vaporized in dynamic mode in a second reactor containing hydrated cyclodextrins. The influence of the various parameters is studied by measuring the level of inclusion of the aromatic compounds in the cyclodextrins. The inclusion step is performed in dynamic and nonstatic mode. Moreover, the application claimed by the authors is quite different since it involves the attachment of volatile molecules by inclusion. Finally, this method is not used with supercritical fluids but with gases under pressure.

Finally, international application WO 03/030867, filed in the name of PIERRE FABRE MEDICAMENT, relates to a method for preparing compounds for interaction of an anilide derivative with a porous support, necessarily comprising the following steps:
a) mixing the anilide derivative generated with supercritical fluid and the determined quantity of porous support,
b) carrying out a molecular diffusion step by bringing a supercritical fluid into contact, in static mode, with the mixture obtained in step a),
c) washing the compound for interaction obtained in step b) with a stream of supercritical fluid, and
d) recovering the particles of the compound for interaction thus formed.

It should be noted that step c) for washing carried out in a supercritical medium is essential since it makes it possible to remove the residual solvents and participates in improving the solubility of the active ingredient.

However, all these methods seem difficult to use for preparing inclusion complexes on an industrial scale.

Surprisingly, the inventors of the present application have discovered that a method comprising a step of molecular diffusion with a dense fluid under pressure, in static mode and free of the subsequent washing step with the aid of a supercritical fluid, significantly improved the level of inclusion as a function of the quantity of diffusion agent added to the medium.

Thus, the present invention relates to a method for the preparation of soluble molecular complexes comprising one or more active substances which are poorly soluble in an aqueous medium, included in one or more host molecules, characterized in that it consists, with limitation, of the following steps:
(a) bringing one or more active substances into contact with one or more host molecules,
(b) carrying out a molecular diffusion step by bringing a dense fluid under pressure into contact, in static mode, with the mixture obtained in step (a) in the presence of one or more diffusion agents,
(c) recovering the molecular complex thus formed.

The expression "dense fluid under pressure" is understood to mean, for the purposes of the present invention, any fluid used at a temperature or a pressure greater than their critical value. Advantageously, it is pure $CO_2$ or $CO_2$ mixed with an organic solvent conventionally used by a person skilled in the art.

The expression "active substance poorly soluble in an aqueous medium" is understood to mean, for the purposes of the present invention, any active substance which is poorly or not soluble in an aqueous medium and having in particular a solubility of less than at least 20 µg/ml. In particular, it may be a pharmaceutical active agent (there may be mentioned by way of example analgesics, antipyretics, aspirin and its derivatives, antibiotics, anti-inflammatory agents, antiulcer agents, antihypertensives, neuroleptics, antidepressants, oligonucleotides having a therapeutic activity, peptides having a therapeutic activity and proteins having a therapeutic activity), a cosmetic active agent or a nutraceutical active agent. Advantageously, it is an active substance chosen from the group comprising anilide derivatives, epipodophyllotoxin derivatives, minoxidil, piroxicam, valeric acid, octanoic acid, lauric acid, stearic acid, tiaprofenic acid, omeprazole and eflucimibe.

The expression "host molecule" is understood to mean, for the purposes of the present invention, any substance capable of capturing active substances. Advantageously, the host molecule is chosen from the group consisting of polysaccharides and monosaccharides, in particular cyclodextrins and a mixture thereof. Advantageously, it is β-cyclodextrin, methyl-β-cyclodextrin, γ-cyclodextrin or hydroxypropyl-β-cyclodextrin.

The expression "diffusion agent" is understood to mean, for the purposes of the present invention, any solvent promoting interaction of the active substance with the host molecule. Advantageously, this diffusion agent is chosen from the group consisting of alcohols, ketones, ethers, esters and water with or without surfactant, and mixtures thereof. More advantageously still, it is water.

The expression "static mode" is understood to mean, for the purposes of the present invention, a reaction or a method in which all the reagents are brought simultaneously into contact and where the reaction is allowed to proceed. For example, in step (b) of the present invention, the active substance(s), water and supercritical $CO_2$ are placed in an autoclave and left to react for several hours. The product mass does not change during the reaction. Conversely, in dynamic mode, the reagents are supplied as the reaction or the production progresses. Often, in the context of a dynamic mode, there is circulation of a fluid or stirring. The product mass changes during the production.

The active substance and the host molecule are introduced in solid or liquid form into a container into which the dense fluid under pressure and the diffusion agent are injected in judiciously chosen proportions. The pressure and temperature conditions and the duration of the treatment are defined, by any appropriate method, according to the nature of the active substance(s) and of the host molecule(s).

Advantageously, step (b) of molecular diffusion of the method according to the present invention is performed with stirring.

The diffusion agent may be added continuously or batchwise in a quantity of between 1 and 50% by mass, preferably between 20 and 25% by mass.

The time necessary for the molecular diffusion of step (b) is determined by any appropriate method. This step (b) may be repeated as often as desired to obtain a satisfactory dissolution rate. Advantageously, step (b) lasts for between about 2 and 16 hours.

The pressure and temperature conditions of step (b) are chosen so as to promote molecular diffusion. Advantageously, the pressure of the supercritical fluid is between 5 MPa and 40 MPa and the temperature is between 0 and 120° C.

Advantageously, step (b) of the method according to the present invention is carried out in a closed reactor, in particular an autoclave.

The method may be carried out batchwise or continuously. Advantageously, the method according to the present invention is carried out batchwise.

The present invention also relates to the soluble molecular complexes comprising one or more active substances which are poorly soluble in an aqueous medium, included in one or more host molecules, characterized in that they are capable of being obtained by the method according to the present invention.

Carrying out the molecular diffusion step in a dense medium under pressure in the presence of a diffusion agent allows a strong interaction of the particles of active substance with the host molecule, which promotes dissolution in aqueous medium, which is multiplied by about 100 by the method according to the present invention.

The following examples for carrying out the method are given as a guide without limitation.

EXAMPLE 1

Minoxidil (Active Substance) and γ-cyclodextrin (Host Molecule)

1.1. Methods for Evaluating the Level of Inclusion

The level of inclusion of the active substance in the host molecule is evaluated by differential scanning calorimetry. A temperature ramp is applied under a nitrogen stream to the test product with the aid of a Perkin Elmer DSC 7 apparatus.

The complexing yield is evaluated by measuring the reduction (or disappearance) of the thermal peak relative to the active ingredient which has remained free.

1.2. Without Addition of Diffusion Agent

One mole of minoxidil and two moles of γ-cyclodextrin are introduced into a reactor. Carbon dioxide is subsequently introduced into the reactor at a pressure of 15 MPa and at a temperature of 80° C. The whole is kept under these operating conditions for a period of two hours.

After decompression of the medium, the inclusion level is measured on the powder collected and is found to be equal to 0%. No inclusion of the active substance can be observed in the host molecule.

1.3. With Addition of Diffusion Agent

One mole of minoxidil and two moles of γ-cyclodextrin are introduced into a reactor, together with 12.1% by mass of diffusion agent (water). Carbon dioxide is subsequently introduced into the reactor at a pressure of 15 MPa and at a temperature of 80° C. The whole is kept under these operating conditions for a period of two hours.

After decompression of the medium, the inclusion level is measured on the powder collected and is found to be equal to 45%.

A second trial was carried out under the same operating conditions as above, the only difference being that the quantity of diffusion agent added was increased to 23.1%.

After decompression of the medium, the inclusion level is measured on the powder collected and is found to be equal to 62%.

EXAMPLE 2

Minoxidil (Active Substance) and methyl-β-cyclodextrin (Host Molecule)

2.1. Without Addition of Diffusion Agent

One mole of minoxidil and two moles of methyl-β-cyclodextrin are introduced into a reactor. Carbon dioxide is subsequently introduced into the reactor at a pressure of 15 MPa and at a temperature of 80° C. The whole is kept under these operating conditions for a period of two hours.

After decompression of the medium, the inclusion level is measured on the powder collected and is found to be equal to 17%.

2.2. With Addition of Diffusion Agent

One mole of minoxidil and two moles of methyl-β-cyclodextrin are introduced into a reactor, together with 8.4% by mass of diffusion agent (water). Carbon dioxide is subsequently introduced into the reactor at a pressure of 15 MPa and at a temperature of 80° C. The whole is kept under these operating conditions for a period of two hours.

After decompression of the medium, the inclusion level is measured on the powder collected and is found to be equal to 60%.

EXAMPLE 3

Piroxicam (Active Substance) and β-cyclodextrin (Host Molecule)

3.1. Without Addition of Diffusion Agent

One mole of piroxicam and two moles of β-cyclodextrin are introduced into a reactor. Carbon dioxide is subsequently introduced into the reactor at a pressure of 15 MPa and at a temperature of 150° C. The whole is kept under these operating conditions for a period of two hours.

After decompression of the medium, the inclusion level is measured on the powder collected and is found to be equal to 0%. No inclusion of the active substance can be observed in the host molecule.

3.2. With Addition of Diffusion Agent

One mole of piroxicam and two moles of β-cyclodextrin are introduced into a reactor, together with 11.8% by mass of diffusion agent (water). Carbon dioxide is subsequently introduced into the reactor at a pressure of 15 MPa and at a temperature of 15° C. The whole is kept under these operating conditions for a period of two hours.

After decompression of the medium, the inclusion level is measured on the powder collected and is found to be equal to 50%.

A second trial was carried out under the same operating conditions as above, the only difference being that the quantity of diffusion agent added was increased to 19.8%.

After decompression of the medium, the inclusion level is measured on the powder collected and is found to be equal to 92%.

EXAMPLE 4

Piroxicam (Active Substance) and γ-cyclodextrin (Host Molecule)

4.1. Without Addition of Diffusion Agent

One mole of piroxicam and two moles of γ-cyclodextrin are introduced into a reactor. Carbon dioxide is subsequently introduced into the reactor at a pressure of 15 MPa and at a temperature of 150° C. The whole is kept under these operating conditions for a period of two hours.

After decompression of the medium, the inclusion level is measured on the powder collected and is found to be equal to 0%. No inclusion of the active substance can be observed in the host molecule.

4.2. With Addition of Diffusion Agent

One mole of piroxicam and two moles of γ-cyclodextrin are introduced into a reactor, together with 22% by mass of diffusion agent (water). Carbon dioxide is subsequently introduced into the reactor at a pressure of 15 MPa and at a temperature of 150° C. The whole is kept under these operating conditions for a period of two hours.

After decompression of the medium, the inclusion level is measured on the powder collected and is found to be equal to 28%.

EXAMPLE 5

Tiaprofenic Acid (Active Substance) and γ-cyclodextrin (Host Molecule)

5.1. Without Addition of Diffusion Agent

One mole of tiaprofenic acid and two moles of γ-cyclodextrin are introduced into a reactor. Carbon dioxide is subsequently introduced into the reactor at a pressure of 15 MPa and at a temperature of 50° C. The whole is kept under these operating conditions for a period of two hours.

After decompression of the medium, the inclusion level is measured on the powder collected and is found to be equal to 19%.

5.2 With Addition of Diffusion Agent

One mole of tiaprofenic acid and two moles of γ-cyclodextrin are introduced into a reactor, together with 20.5% by mass of diffusion agent (water). Carbon dioxide is subsequently introduced into the reactor at a pressure of 15 MPa and at a temperature of 50° C. The whole is kept under these operating conditions for a period of two hours.

After decompression of the medium, the inclusion level is measured on the powder collected and is found to be equal to 100%. The inclusion of the active substance in the host molecule appears to be complete in this case.

EXAMPLE 6

Omeprazole (Active Substance) and γ-cyclodextrin (Host Molecule)

6.1. Without addition of diffusion agent

One mole of omeprazole and two moles of γ-cyclodextrin are introduced into a reactor. Carbon dioxide is subsequently introduced into the reactor at a pressure of 15 MPa and at a temperature of 100° C. The whole is kept under these operating conditions for a period of two hours.

After decompression of the medium, the inclusion level is measured on the powder collected and is found to be equal to 2%. Without addition of diffusion agent, the inclusion of the active substance in the host molecule appears to be very low.

6.2. With Addition of Diffusion Agent

One mole of omeprazole and two moles of γ-cyclodextrin are introduced into a reactor, together with 20.7% by mass of diffusion agent. Carbon dioxide is subsequently introduced into the reactor at a pressure of 15 MPa and at a temperature of 100° C. The whole is kept under these operating conditions for a period of two hours.

After decompression of the medium, the inclusion level is measured on the powder collected and is found to be equal to 66%.

EXAMPLE 7

Eflucimibe (Active Substance) and γ-cyclodextrin (Host Molecule)

7.1. Without Addition of Diffusion Agent

One mole of eflucimibe and two moles of γ-cyclodextrin are introduced into a reactor. Carbon dioxide is subsequently introduced into the reactor at a pressure of 30 MPa and at a temperature of 100° C. The whole is kept under these operating conditions for a period of sixteen hours.

After decompression of the medium, the inclusion level is measured on the powder collected and is found to be equal to 0%. Without addition of diffusion agent, the inclusion of the active substance in the host molecule is zero.

7.2. With Addition of Diffusion Agent

One mole of eflucimibe and two moles of γ-cyclodextrin are introduced into a reactor, together with 25% by mass of diffusion agent (water). Carbon dioxide is subsequently introduced into the reactor at a pressure of 30 MPa and at a temperature of 100° C. The whole is kept under these operating conditions for a period of two hours.

After decompression of the medium, the inclusion level is measured on the powder collected and is found to be equal to 60%.

7.3. Dissolution Test

A dissolution test was performed on the products obtained in examples 7.1 and 7.2.

After stirring for 2 hours in a 5% sodium lauryl sulfate solution, the quantity of eflucimibe solubilized from the powder collected in example 7.1 is 24 µg/ml instead of 22 µg/ml for the initial mixture.

After stirring for 2 hours in a 5% sodium lauryl sulfate solution, the quantity of eflucimibe solubilized from the powder collected in example 7.2 is 160 µg/ml instead of 22 µg/ml for the initial mixture.

All the results given above show the major importance of the addition of a diffusion agent in order to improve the level of inclusion of the active substance in the host molecule and consequently the dissolution in water.

The invention claimed is:

1. A method for the preparation of soluble molecular complexes, said method consisting essentially of:
    (a) mixing one or more active substances which are poorly soluble in an aqueous medium with one or more host molecule components selected from the group consisting of β-cyclodextrin, methyl-β-cyclodextrin, γ-cyclodextrin, and hydroxypropyl-β-cyclodextrin, and separately adding water as a diffusion agent in an amount of between 8.4% and 50% by mass of the entire mixture in the absence of an organic solvent;
    (b) carrying out a molecular diffusion step by bringing supercritical carbon dioxide under pressure into contact, in static mode, with the mixture obtained in step (a), wherein the pressure is between 5 MPa and 40 MPa and the temperature is between 0 and 120° C., thereby forming a molecular complex; and
    (c) recovering the molecular complex.

2. A method as claimed in claim 1, wherein the molecular diffusion step (b) is carried out for 2 hours.

3. The method as claimed in claim 1, wherein step (b) of molecular diffusion is performed with stirring.

4. The method as claimed in claim 1, wherein the active substance is a pharmaceutical active agent, a cosmetic active agent, or a nutraceutical active agent.

5. The method as claimed in claim 4, wherein the active substance is selected from the group consisting of anilides, epipodophyllotoxin, minoxidil, piroxicam, valeric acid, octanoic acid, lauric acid, stearic acid, tiaprofenic acid, omeprazole, and eflucimibe.

6. The method as claimed in claim 4, wherein the active substance is a pharmaceutical active agent selected from the group consisting of analgesics, antipyretics, aspirin, antibiotics, anti-inflammatory agents, antiulcer agents, antihypertensives, neuroleptics, antidepressants, oligonucleotides having a therapeutic activity, peptides having a therapeutic activity, and proteins having a therapeutic activity.

* * * * *